(12) United States Patent
Shinbo

(10) Patent No.: US 7,678,871 B2
(45) Date of Patent: Mar. 16, 2010

(54) PREPARATION OF CYCLIC OLIGOSILOXANE

(75) Inventor: Kouichi Shinbo, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 461 days.

(21) Appl. No.: 11/277,855

(22) Filed: Mar. 29, 2006

(65) Prior Publication Data

US 2006/0223963 A1 Oct. 5, 2006

(30) Foreign Application Priority Data

Mar. 30, 2005 (JP) .............................. 2005-097780

(51) Int. Cl.
C08G 77/06 (2006.01)
C08G 77/12 (2006.01)

(52) U.S. Cl. .......................................... 528/16; 528/31

(58) Field of Classification Search .................. None
See application file for complete search history.

(56) References Cited

U.S. PATENT DOCUMENTS

| 4,078,104 | A | * | 3/1978 | Martin | 427/387 |
| 4,447,630 | A |   | 5/1984 | Williams, Jr. | |
| 5,491,249 | A |   | 2/1996 | Kostas | |
| 5,663,269 | A | * | 9/1997 | Chu et al. | 528/14 |
| 5,698,653 | A | * | 12/1997 | Lucas et al. | 528/17 |
| 5,861,472 | A | * | 1/1999 | Cifuentes et al. | 525/477 |
| 6,265,514 | B1 | * | 7/2001 | Warren et al. | 528/24 |

FOREIGN PATENT DOCUMENTS

| EP | 0 361 274 A2 | 4/1990 |
| EP | 0 990 660 A1 | 4/2000 |
| JP | 54-74900 | 6/1979 |
| JP | 60-90220 | 5/1985 |
| JP | 7-316167 | 12/1995 |
| JP | 2000-159783 | 6/2000 |
| JP | 2000-159784 | 6/2000 |
| JP | 2000-169488 | 6/2000 |

OTHER PUBLICATIONS

Abstract of JP 3-95227, Apr. 19, 1991.*
K. A. Andrianov, et al., "Synthesis of New Polymers with Inorganic Chains of Molecules", Journal of Polymer Science, vol. XXX, 1958, pp. 513-524.
J. V. Crivello, et al., "Synthesis of Cyclic Siloxanes by the Thermal Depolymerization of Linear Poly (siloxanes)", Chemistry of Materials, vol. 1, No. 4, XP-002390282, 1989, pp. 445-451.
Shixuan Xin, et al., "Redistribution reactions of alkoxy-and siloxysilanes, catalyzed by dimethyltitanocene", Canadian Journal of Chemistry, vol. 68, No. 3, XP-009069429, 1990, pp. 471-476.
Joseph B. Lambert, et al., "Redistribution of Cyclosiloxanes to Favor Formation of Decamethylcyclopentasiloxane", Journal of Polymer Science, Part A: Polymer Chemistry, vol. 31, No. 7, XP-009069406, 1993, pp. 1697-1700.

* cited by examiner

*Primary Examiner*—Marc S Zimmer
(74) *Attorney, Agent, or Firm*—Oblon, Spivak, McClelland, Maier & Neustadt, L.L.P.

(57) ABSTRACT

Cyclic oligosiloxane is prepared through disproportionation reaction of organopolysiloxane in the presence of a catalyst. Cyclic oligosiloxane of high purity can be produced in high yields by using a catalyst having formula (4):

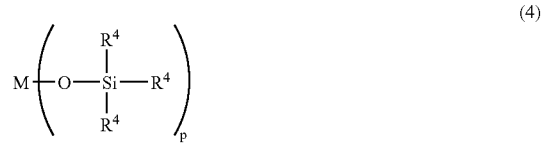

(4)

wherein M is Al, Ti, Zr, Sn or Zn, p is the valence of M, and $R^4$ is a monovalent hydrocarbon group or the like.

7 Claims, No Drawings

PREPARATION OF CYCLIC OLIGOSILOXANE

CROSS-REFERENCE TO RELATED APPLICATION

This non-provisional application claims priority under 35 U.S.C. §119(a) on patent application Ser. No. 2005-097780 filed in Japan on Mar. 30, 2005, the entire contents of which are hereby incorporated by reference.

TECHNICAL FIELD

This invention relates to a method for preparing cyclic oligosiloxanes from high molecular weight organopolysiloxanes.

BACKGROUND ART

Cyclic oligosiloxanes are used as the raw material for high molecular weight polysiloxanes such as silicone fluid and gum, and when having Si—H bonds, as the raw material for organohydrogenpolysiloxanes, the raw material for adhesive aids having organic functional groups bonded thereto, and the like.

One process known in the art for the preparation of cyclic oligosiloxanes is by hydrolysis of a silane having two hydrolyzable groups such as dimethyldichlorosilane, as described in JP-A 54-74900 and U.S. Pat. No. 4,447,630 (JP-A 60-90220). When it is desired to selectively produce a cyclic oligosiloxane during hydrolysis, the co-presence of alcohol during hydrolysis is a common practice, leaving the problems of low pot yields and increased BOD loads due to the inclusion of alcohol in the water discharge. When the desired cyclic oligosiloxane is recovered from the silane hydrolyzate, fractional distillation is necessary, resulting in an extended manufacture process.

It is known from JP-A 2000-159783, JP-A 2000-159784, and JP-A 2000-169488 that cyclic oligosiloxanes are produced through disproportionation reaction of high molecular weight siloxanes in the presence of catalysts.

The methods described in these patents use metal alkoxides as the catalyst for helping produce cyclic oligosiloxanes under milder conditions. During the process, however, molecules having a silicon-alkoxide bond originating from the metal alkoxide catalyst form in addition to the cyclic oligosiloxane. When the oligosiloxane produced is used as the raw material, these molecules become impurities adversely affecting the properties of the end product. A high-performance fractional distillation unit is necessary for separating the molecules having a silicon-alkoxide bond from the cyclic oligosiloxane.

JP-A 7-316167 discloses the use of anhydrous aluminum chloride catalyst for producing cyclic tetramer siloxane. The anhydrous aluminum chloride suffers from extreme difficulty of handling and a likelihood of generating hydrochloric acid in the system.

DISCLOSURE OF THE INVENTION

An object of the present invention is to provide a method for preparing cyclic oligosiloxanes of high purity in high yields from high molecular weight siloxanes.

The invention relates to a process for producing cyclic oligosiloxane through disproportionation reaction of high molecular weight organopolysiloxane in the presence of a catalyst. The inventor has found that production of cyclic oligosiloxane of high purity in high yields can be achieved by using a catalyst having the general formula (4):

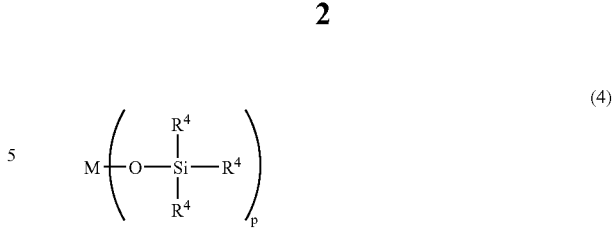

wherein M is a metal selected from among aluminum, titanium, zirconium, tin and zinc, p is the valence of the metal M, and $R^4$ is each independently a substituted or unsubstituted monovalent hydrocarbon group or a group of the formula (5):

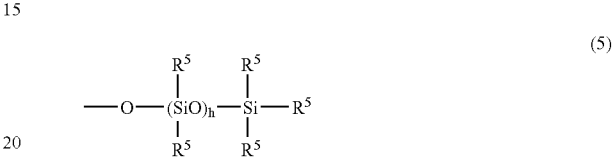

wherein $R^5$ is each independently a substituted or unsubstituted monovalent hydrocarbon group and h is an integer of 0 to 100.

The use of the catalyst having formula (4) not only ensures that cyclic oligosiloxane of high purity is produced in high yields from high molecular weight organopolysiloxane without leaving BOD loads, but also minimizes formation of molecules having a silicon-alkoxide bond which are problematic in the semiconductor and electric/electronic applications.

As discussed above, in one prior art process wherein the desired cyclic oligosiloxane is recovered from a hydrolyzate of a silane having two hydrolyzable groups, fractional distillation is necessary. In the other prior art process, when it is desired to selectively produce the desired cyclic oligosiloxane, the inclusion of alcohol during hydrolysis is a common practice, leaving the problems of low pot yields and increased BOD loads of the water discharge. In the further prior art process wherein cyclic oligosiloxane is produced through disproportionation reaction of high molecular weight siloxane in the presence of metal alkoxide catalyst, additional molecules having a silicon-alkoxide bond form and are difficult to separate from the desired cyclic oligosiloxane. If the cyclic oligosiloxane contaminated with such molecules is used as the raw material in a subsequent process, they can have negative impact on the properties of the end product. Making extensive investigations to avoid formation of silicon-alkoxide molecules in the process of preparing cyclic oligosiloxane from high molecular weight siloxane in the presence of a catalyst, the inventor has discovered that a catalyst of formula (4) has an outstanding capability of avoiding formation of silicon-alkoxide molecules.

The invention provides a method for preparing a cyclic oligosiloxane having the general formula (3), comprising reacting an organopolysiloxane having the general formula (1) and/or an organopolysiloxane having the general formula (2) in the presence of a catalyst wherein the catalyst has the general formula (4).

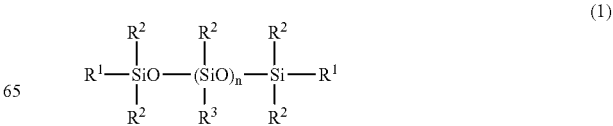

-continued

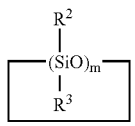 (2)

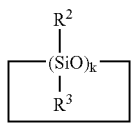 (3)

Herein $R^1$ is each independently hydrogen, hydroxyl or a substituted or unsubstituted monovalent hydrocarbon group, $R^2$ is each independently a substituted or unsubstituted monovalent hydrocarbon group, $R^3$ is hydrogen or a substituted or unsubstituted monovalent hydrocarbon group, n is an integer of 2 to 10,000, m is an integer of 4 to 15, and k is an integer of 3 to 8, with the proviso that k<m when the organopolysiloxane of formula (2) is used.

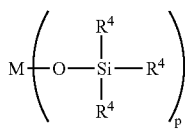 (4)

Herein M is a metal selected from among aluminum, titanium, zirconium, tin and zinc, p is the valence of the metal M, and $R^4$ is each independently a substituted or unsubstituted monovalent hydrocarbon group or a group of the formula (5):

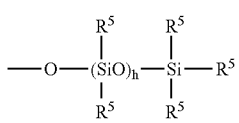 (5)

wherein $R^5$ is each independently a substituted or unsubstituted monovalent hydrocarbon group and h is an integer of 0 to 100.

In a preferred embodiment, the catalyst is present in an amount of 0.001 to 10 parts by weight per 100 parts by weight of the starting organopolysiloxane(s).

In another preferred embodiment, the catalyst has the general formula (4a):

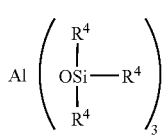 (4a)

wherein $R^4$ is as defined above.

In a further preferred embodiment, the cyclic oligosiloxane has the general formula (3a):

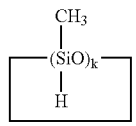 (3a)

wherein k is as defined above.

In a further preferred embodiment, the cyclic oligosiloxane has the general formula (3b):

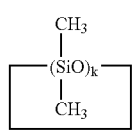 (3b)

wherein k is as defined above.

The method of the present invention is successful in producing cyclic oligosiloxane without forming impurities such as molecules having a silicon-alkoxide bond. Thus the cyclic oligosiloxane of high purity is obtained in high yields.

DESCRIPTION OF THE PREFERRED EMBODIMENTS

The method for preparing cyclic oligosiloxane according to the invention is by reacting an organopolysiloxane having the general formula (1) and/or an organopolysiloxane having the general formula (2) in the presence of a catalyst.

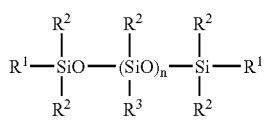 (1)

Herein $R^1$ is each independently hydrogen, hydroxyl or a substituted or unsubstituted monovalent hydrocarbon group, $R^2$ is each independently a substituted or unsubstituted monovalent hydrocarbon group, $R^3$ is hydrogen or a substituted or unsubstituted monovalent hydrocarbon group, and n is an integer of 2 to 10,000.

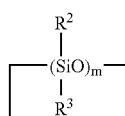 (2)

Herein $R^2$ is each independently a substituted or unsubstituted monovalent hydrocarbon group, $R^3$ is hydrogen or a substituted or unsubstituted monovalent hydrocarbon group, and m is an integer of 4 to 15.

More particularly, $R^1$ which may be the same or different is a hydrogen atom, a hydroxyl group or a substituted or unsubstituted monovalent hydrocarbon group. Suitable monovalent hydrocarbon groups include those of 1 to 12 carbon atoms, preferably 1 to 10 carbon atoms, for example, alkyl groups such as methyl, ethyl, n-propyl, isopropyl, n-butyl, isobutyl and t-butyl, cycloalkyl groups such as cyclohexyl, alkenyl groups such as vinyl, allyl and propenyl, aryl groups such as phenyl and tolyl, aralkyl groups such as benzyl and phenylethyl, and substituted forms of the foregoing groups in which one or more hydrogen atoms are substituted by halogen atoms or the like, such as 3,3,3-trifluoropropyl. Of these, hydrogen, methyl and phenyl are preferred, with the methyl and hydrogen being most preferred. Methyl and hydrogen are preferred particularly when $R^3$ is hydrogen, and methyl is preferred particularly when $R^3$ is a monovalent hydrocarbon group.

$R^2$ which may be the same or different is a substituted or unsubstituted monovalent hydrocarbon group, examples of which are the same as described for $R^1$. Inter alia, methyl and phenyl are preferred, with the methyl being most preferred.

$R^3$ is a hydrogen atom or a substituted or unsubstituted monovalent hydrocarbon group, examples of which are the same as described for $R^1$. Inter alia, hydrogen, methyl and phenyl are preferred, with the hydrogen and methyl being most preferred.

In formula (1), n is an integer of 2 to 10,000, preferably 10 to 2,000, more preferably 20 to 1,500. In formula (2), m is an integer of 4 to 15, preferably 4 to 10.

The method for preparing cyclic oligosiloxane according to the invention favors use of an organopolysiloxane having formula (1) as the starting reactant. In preparing the organopolysiloxane having formula (1), an organopolysiloxane having formula (2) can also be formed. The resulting organopolysiloxane mixture may be used without separation. In this mixture, the organopolysiloxane having formula (1) and the organopolysiloxane having formula (2) are present preferably in a ratio from 100:0 to 20:80, and more preferably from 100:0 to 30:70 by weight.

For reaction of the reactants, organopolysiloxanes having formula (1) and/or (2), a catalyst having the general formula (4) is used.

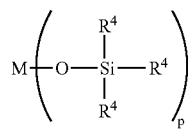
(4)

Herein M is a metal selected from among aluminum, titanium, zirconium, tin and zinc, p is the valence of the metal M, and $R^4$ is each independently a substituted or unsubstituted monovalent hydrocarbon group or a group of the formula (5).

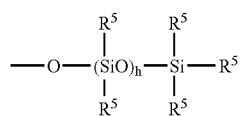
(5)

Herein $R^5$ is each independently a substituted or unsubstituted monovalent hydrocarbon group. Examples of monovalent hydrocarbon groups represented by $R^5$ are as will be described for $R^4$, and are typically methyl, ethyl, propyl and phenyl, with methyl being most preferred. The subscript h is an integer of 0 to 100, preferably 0 to 50, and more preferably 0 to 20.

In formula (4), $R^4$ which may be the same or different is a substituted or unsubstituted monovalent hydrocarbon group, preferably of 1 to 12 carbon atoms, more preferably 1 to 10 carbon atoms. Examples include alkyl groups such as methyl, ethyl, n-propyl, isopropyl, n-butyl, isobutyl and t-butyl, cycloalkyl groups such as cyclohexyl, alkenyl groups such as vinyl, allyl and propenyl, aryl groups such as phenyl and tolyl, aralkyl groups such as benzyl and phenylethyl, and substituted forms of the foregoing groups in which one or more hydrogen atoms are substituted by halogen atoms or the like, such as 3,3,3-trifluoropropyl. Of these, alkyl groups of 1 to 4 carbon atoms and phenyl are preferred, with methyl being most preferred.

M is as defined above, with aluminum being preferred.

Illustrative examples of the catalyst having formula (4) are given below.

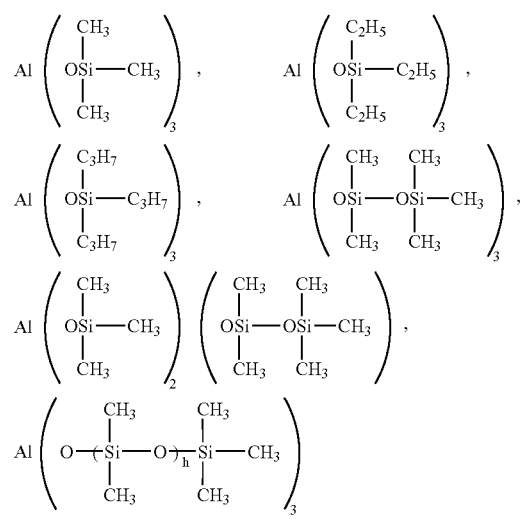

Note that h is as defined above.

No particular limit is imposed on the technique of preparing the catalyst having formula (4). It may be prepared by the technique described in A. A. Zhdanov, J. Polymer Sci., 30, 513 (1958), for example.

An appropriate amount of the catalyst having formula (4) is 0.001 to 10 parts by weight, more preferably 0.01 to 5 parts by weight per 100 parts by weight of the reactants, organopolysiloxanes having formula (1) and/or (2).

In the method of the invention, the reaction is preferably carried out at a temperature of room temperature to 250° C., more preferably 130° C. to 200° C., when $R^3$ is hydrogen, and at a temperature of 200° C. to 350° C., more preferably 240° C. to 300° C., when $R^3$ is a monovalent hydrocarbon group. Also, the reaction may be carried out either under atmospheric pressure or under reduced pressure, preferably under a reduced pressure of up to 500 mmHg, more preferably 10 to 300 mmHg. If necessary, the reaction is followed by distillation.

The disproportionation reaction according to the invention produces a cyclic oligosiloxane having the general formula (3):

(3)

Herein $R^2$ is each independently a substituted or unsubstituted monovalent hydrocarbon group, $R^3$ is hydrogen or a substituted or unsubstituted monovalent hydrocarbon group, k is an integer of 3 to 8, preferably 4 to 6, with the proviso that k<m when the organopolysiloxane of formula (2) is used. Understandably, the cyclic oligosiloxane is generally produced as a mixture of cyclic oligosiloxanes having different degrees of polymerization.

EXAMPLE

Examples and Comparative Examples are given below for further illustrating the invention, but are not intended to limit the invention.

Catalyst Synthesis

A catalyst having formula (i) was synthesized according to the teaching of A. A. Zhdanov, J. Polymer Sci., 30, 513 (1958).

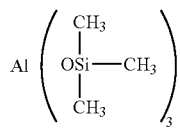
(i)

A 0.5-L three-necked flask equipped with a stirrer and condenser was charged with 40 g of sodium trimethylsilanolate, after which 160 mL of benzene was added for dissolving the silanolate. At room temperature, a suspension of 12.4 g of aluminum chloride in 70 mL of benzene was added over one hour whereby the temperature increased from 20° C. to 40° C. At the end of the exothermic reaction, the reaction solution was filtered through a paper filter. The filtrate was added to a 1-L flask which was heated in an oil bath, distilling off the benzene at atmospheric pressure. The solidified flask contents were purified by sublimation under vacuum, obtaining the target substance. Its structure was identified by proton-NMR.

Example 1

A 1-L four-necked flask equipped with a thermometer, stirrer, column packed with cylindrical glass of about 1×1 mm to a height of 500 mm, water-cooled condenser, outlet tube, and distillate receiver was connected to a vacuum pump. To the flask were fed 500 g of trimethylsilyl end-capped polymethylhydrogensiloxane having the formula:

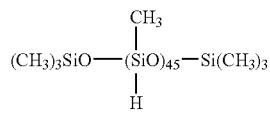

and 0.5 g of the catalyst (i) synthesized above, after which agitation was commenced. While the flask interior was kept under a reduced pressure of 50 mmHg, the flask was heated at 170-180° C. in an oil bath. A fraction that distilled out for 2 hours was collected (398 g). The majority of this fraction was 1,3,5,7-tetramethylcyclotetrasiloxane. The residue (40 g) was a clear liquid.

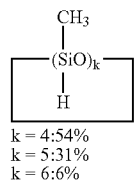

k = 4:54%
k = 5:31%
k = 6:6%

Example 2

A 1-L four-necked flask equipped with a thermometer, stirrer, column packed with cylindrical glass of about 1×1 mm to a height of 500 mm, water-cooled condenser, outlet tube, and distillate receiver was connected to a vacuum pump. To the flask were fed 500 g of trimethylsilyl end-capped polymethylhydrogensiloxane having the formula:

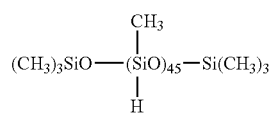

and 0.1 g of the catalyst (i) synthesized above, after which agitation was commenced. While the flask interior was kept under a reduced pressure of 100 mmHg, the flask was heated at 160-170° C. in an oil bath. A fraction that distilled out for 2 hours was collected (356 g). The majority of this fraction was 1,3,5,7-tetramethylcyclotetrasiloxane. The residue (129 g) was a clear liquid.

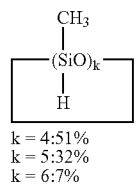

k = 4:51%
k = 5:32%
k = 6:7%

Example 3

A 1-L four-necked flask equipped with a thermometer, stirrer, column packed with cylindrical glass of about 1×1 mm to a height of 500 mm, water-cooled condenser, outlet tube, and distillate receiver was connected to a vacuum pump. To the flask were fed 100 g of trimethylsiloxy end-capped dimethylpolysiloxane having a viscosity of 10,000 centistokes at 25° C. and 1.0 g of the catalyst (i) synthesized above, after which agitation was commenced. While the flask interior was kept under a reduced pressure of 50 mmHg, the flask was heated at 250-260° C. using a mantle heater. A fraction that distilled out for 14 hours was collected (45 g). The residue (31 g) was a clear liquid.

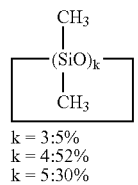

k = 3:5%
k = 4:52%
k = 5:30%

Comparative Example 1

A 1-L four-necked flask equipped with a thermometer, stirrer, column packed with cylindrical glass of about 1×1 mm to a height of 500 mm, water-cooled condenser, outlet tube, and distillate receiver was connected to a vacuum pump. To the flask were fed 500 g of trimethylsilyl end-capped polymethylhydrogensiloxane having the formula:

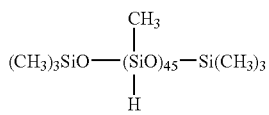

and 0.1 g of a catalyst $Al(OR)_3$ wherein R is isopropyl, after which agitation was commenced. While the flask interior was kept under a reduced pressure of 100 mmHg, the flask was heated at 160-170° C. in an oil bath. A fraction that distilled out for 2 hours was collected (460 g). The majority of this fraction was 1,3,5,7-tetramethylcyclotetrasiloxane.

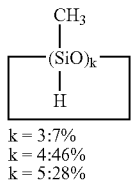

k = 3:7%
k = 4:46%
k = 5:28%

An analysis by gas chromatography revealed that by-products having added thereto an isopropoxide group originating from the catalyst, represented by the following formulae (a) and (b), formed in amounts of about 1.5% and about 0.5%, respectively. The residue (32 g) was a clear liquid.

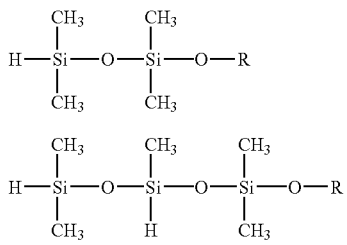

Note that R is isopropyl.

In none of Examples 1 to 3, an alkoxy group bonded to Si was detected on analysis of the fractions by gas chromatography.

Japanese Patent Application No. 2005-097780 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for preparing a cyclic oligosiloxane, comprising reacting an organopolysiloxane having formula (1):

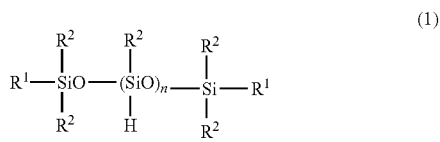

wherein each $R^1$ is independently a substituted or unsubstituted monovalent hydrocarbon group, each $R^2$ is independently a substituted or unsubstituted monovalent hydrocarbon group, and n is an integer of 20 to 10,000, in the presence of a catalyst, the cyclic oligosiloxane prepared having formula (3):

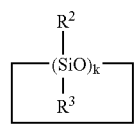

wherein each $R^2$ is independently a substituted or unsubstituted monovalent hydrocarbon group, and k is an integer of 3 to 8, wherein said catalyst has the formula (4):

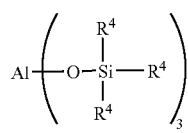

wherein each $R^4$ is independently a substituted or unsubstituted monovalent hydrocarbon group or a group of the formula (5):

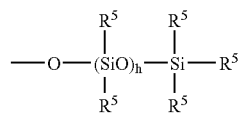

wherein each $R^5$ is independently a substituted or unsubstituted monovalent hydrocarbon group and h is an integer of 0 to 100, whereby the cyclic oligosilxane is produced without forming impurities having a silicon-alkoxide bond.

2. The method of claim 1, wherein said catalyst is present in an amount of 0.001 to 10 parts by weight per 100 parts by weight of the starting organopolysiloxane(s).

3. The method of claim 1, wherein h is an integer of 0 to 50.

4. The method of claim 1, wherein h is an integer of 0 to 20.

5. The method of claim 1, wherein said catalyst is one or more members selected from the group consisting of

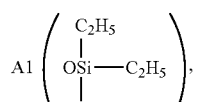
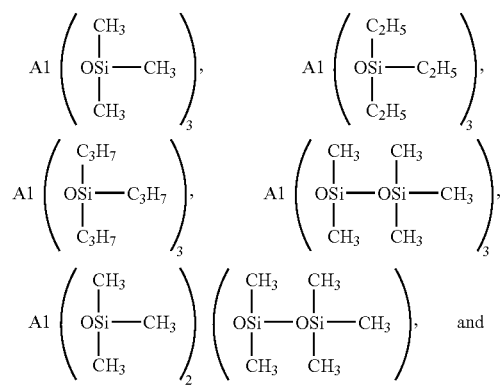
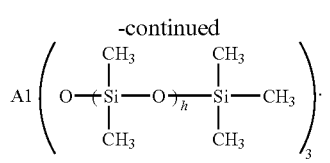
6. The method of claim 1, wherein said catalyst is present in an amount of 0.01 to 5 parts by weight per 100 parts by weight of the starting organopolysiloxane(s).
7. The method of claim 1, wherein k is an integer of 4 to 6.
* * * * *